United States Patent
Sanderson

(10) Patent No.: US 9,938,266 B2
(45) Date of Patent: Apr. 10, 2018

(54) SELECTIVE BACE1 INHIBITORS

(71) Applicant: Eli Lilly and Company, Indianapolis, IN (US)

(72) Inventor: Adam Jan Sanderson, Surrey (GB)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 15/549,674

(22) PCT Filed: Mar. 11, 2016

(86) PCT No.: PCT/US2016/021901
§ 371 (c)(1),
(2) Date: Aug. 9, 2017

(87) PCT Pub. No.: WO2016/149057
PCT Pub. Date: Sep. 22, 2016

(65) Prior Publication Data
US 2018/0030044 A1 Feb. 1, 2018

Related U.S. Application Data

(60) Provisional application No. 62/135,270, filed on Mar. 19, 2015.

(51) Int. Cl.
*A61K 31/54* (2006.01)
*C07D 417/14* (2006.01)
*C07D 279/08* (2006.01)
*A61K 31/5415* (2006.01)

(52) U.S. Cl.
CPC ........ *C07D 417/14* (2013.01); *A61K 31/5415* (2013.01); *C07D 279/08* (2013.01)

(58) Field of Classification Search
CPC .......................... A61K 31/5415; C07D 279/08
USPC ......................... 514/224.2; 544/48
See application file for complete search history.

(56) References Cited

U.S. PATENT DOCUMENTS

| | | |
|---|---|---|
| 8,158,620 B2 | 4/2012 | Suzuki et al. |
| 8,278,441 B2 | 10/2012 | Mergott et al. |
| 8,637,504 B2 | 1/2014 | Hori et al. |
| 9,522,923 B2 | 12/2016 | Richards et al. |
| 2009/0209755 A1 | 8/2009 | Suzuki et al. |

FOREIGN PATENT DOCUMENTS

| | | |
|---|---|---|
| WO | 2011/005738 A1 | 1/2011 |
| WO | 2015/156421 A1 | 10/2015 |

OTHER PUBLICATIONS

Patent Cooperation Treaty International Search Report Authority pertaining to International Application No. PCT/US2016/021901 dated Apr. 22, 2016.
Patent Cooperation Treaty Written Opinion pertaining to International Application No. PCT/US2016/021901 dated Apr. 22, 2016.
Oehlrich, D. Bioorg. Med. Chem. Letters, vol. 24, pp. 2033-2045 (2014).

*Primary Examiner* — Jeffrey H Murray
(74) *Attorney, Agent, or Firm* — Nelsen Lentz

(57) ABSTRACT

The present invention provides a compound of Formula I: or a pharmaceutically acceptable salt thereof.

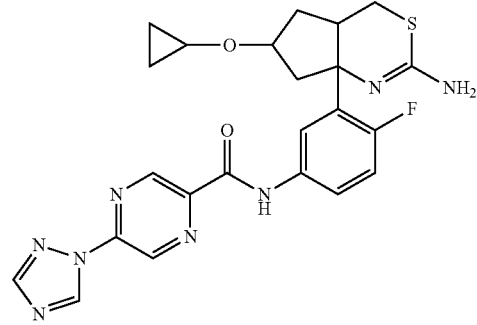

Formula I

6 Claims, No Drawings

SELECTIVE BACE1 INHIBITORS

The present invention relates to novel selective BACE1 inhibitors, to pharmaceutical compositions comprising the compounds, to methods of using the compounds to treat physiological disorders, and to intermediates and processes useful in the synthesis of the compounds.

The present invention is in the field of treatment of Alzheimer's disease and other diseases and disorders involving amyloid β (Abeta) peptide, a neurotoxic and highly aggregatory peptide segment of the amyloid precursor protein (APP). Alzheimer's disease is a devastating neurodegenerative disorder that affects millions of patients worldwide. In view of the currently approved agents on the market which afford only transient, symptomatic benefits to the patient rather than halting, slowing, or reversing the disease, there is a significant unmet need in the treatment of Alzheimer's disease.

Alzheimer's disease is characterized by the generation, aggregation, and deposition of Abeta in the brain. Complete or partial inhibition of β-secretase (β-site amyloid precursor protein-cleaving enzyme; BACE) has been shown to have a significant effect on plaque-related and plaque-dependent pathologies in mouse models suggesting that even small reductions in Abeta peptide levels might result in a long-term significant reduction in plaque burden and synaptic deficits, thus providing significant therapeutic benefits, particularly in the treatment of Alzheimer's disease. In addition, two homologs of BACE have been identified which are referred to as BACE1 and BACE2, and it is believed that BACE1 is the most clinically important to development of Alzheimer's disease. BACE1 is mainly expressed in the neurons while BACE2 has been shown to be expressed primarily in the periphery. (See D. Oehlrich, *Bioorg. Med. Chem. Lett.*, 24, 2033-2045 (2014)) In addition, BACE2 may be important to pigmentation as it has been identified as playing a role in the processing of pigment cell-specific melanocyte protein (See L. Rochin, et al., *Proc. Natl. Acad. Sci. USA,* 110(26), 10658-10663 (2013)). BACE inhibitors with central nervous system (CNS) penetration, particularly inhibitors that are selective for BACE1 over BACE2 are desired to provide treatments for Abeta peptide-mediated disorders, such as Alzheimer's disease.

U.S. Pat. No. 8,158,620 discloses fused aminodihydrothiazine derivatives which possess BACE1 inhibitory activity and are further disclosed as useful therapeutic agents for a neurodegenerative disease caused by Abeta peptide, such as Alzheimer's type dementia. In addition, U.S. Pat. No. 8,278,441 discloses BACE inhibitors for treatment of diseases and disorders involving Abeta peptide, such as Alzheimer's disease.

The present invention provides certain novel compounds that are inhibitors of BACE. In addition, the present invention provides certain novel compounds that are selective inhibitors of BACE1 over BACE2. Furthermore, the present invention provides certain novel compounds which penetrate the CNS. The present invention also provides certain novel compounds which have the potential for an improved side-effect profile, for example through selective inhibition of BACE1 over BACE2.

Accordingly, the present invention provides a compound of Formula I:

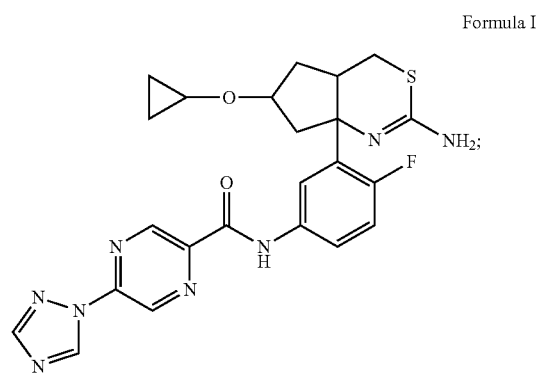 [SMILES: NC1=NC2(c3cc(NC(=O)c4cnc(-n5cncn5)cn4)ccc3F)CC(OC3CC3)CC2CS1]

Formula I or a pharmaceutically acceptable salt thereof.

In addition, the present invention provides a compound of Formula Ia:

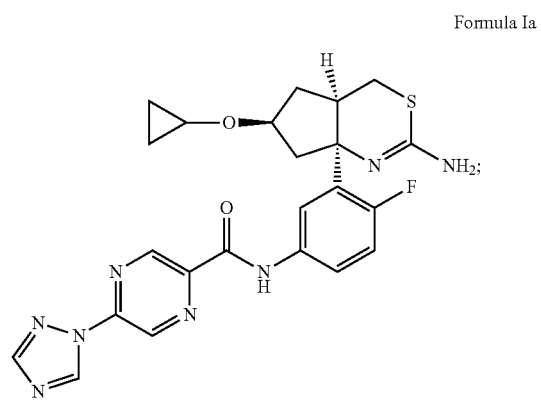 [SMILES: NC1=N[C@@]2(c3cc(NC(=O)c4cnc(-n5cncn5)cn4)ccc3F)C[C@@H](OC3CC3)C[C@H]2CS1]

Formula Ia or a pharmaceutically acceptable salt thereof.

The present invention also provides a method of treating Alzheimer's disease in a patient, comprising administering to a patient in need of such treatment an effective amount of a compound of Formulas I or Ia, or a pharmaceutically acceptable salt thereof.

The present invention further provides a method of preventing the progression of mild cognitive impairment to Alzheimer's disease in a patient, comprising administering to a patient in need of such treatment an effective amount of a compound of Formulas I or Ia, or a pharmaceutically acceptable salt thereof. The present invention also provides a method of inhibiting BACE in a patient, comprising administering to a patient in need of such treatment an effective amount of a compound of Formulas I or Ia, or a pharmaceutically acceptable salt thereof. The present invention also provides a method for inhibiting BACE-mediated cleavage of amyloid precursor protein, comprising administering to a patient in need of such treatment an effective amount of a compound of Formulas I or Ia, or a pharmaceutically acceptable salt thereof. The invention further provides a method for inhibiting production of Abeta peptide, comprising administering to a patient in need of such treatment an effective amount of a compound of Formulas I or Ia, or a pharmaceutically acceptable salt thereof.

Furthermore, this invention provides a compound of Formulas I or Ia, or a pharmaceutically acceptable salt thereof for use in therapy, in particular for the treatment of Alzheimer's disease or for preventing the progression of mild cognitive impairment to Alzheimer's disease. Even furthermore, this invention provides the use of a compound of Formulas I or Ia, or a pharmaceutically acceptable salt thereof, for the manufacture of a medicament for the treatment of Alzheimer's disease.

The invention further provides a pharmaceutical composition, comprising a compound of Formulas I or Ia, or a pharmaceutically acceptable salt thereof, with one or more pharmaceutically acceptable carriers, diluents, or excipients. The invention further provides a process for preparing a pharmaceutical composition, comprising admixing a compound of Formulas I or Ia, or a pharmaceutically acceptable salt thereof, with one or more pharmaceutically acceptable carriers, diluents, or excipients. This invention also encompasses novel intermediates and processes for the synthesis of the compounds of Formulas I and Ia.

Mild cognitive impairment has been defined as a potential prodromal phase of dementia associated with Alzheimer's disease based on clinical presentation and on progression of patients exhibiting mild cognitive impairment to Alzheimer's dementia over time. (Morris, et al., *Arch. Neurol.*, 58, 397-405 (2001); Petersen, et al., *Arch. Neurol.*, 56, 303-308 (1999)). The term preventing the progression of mild cognitive impairment to Alzheimer's disease" includes restraining, slowing, stopping, or reversing the progression of mild cognitive impairment to Alzheimer's disease in a patient.

As used herein, the terms "treating" or "to treat" includes restraining, slowing, stopping, or reversing the progression or severity of an existing symptom or disorder.

As used herein, the term "patient" refers to a human.

The term "inhibition of production of Abeta peptide" is taken to mean decreasing of in vivo levels of Abeta peptide in a patient.

As used herein, the term "effective amount" refers to the amount or dose of compound of the invention, or a pharmaceutically acceptable salt thereof which, upon single or multiple dose administration to the patient, provides the desired effect in the patient under diagnosis or treatment.

An effective amount can be readily determined by the attending diagnostician, as one skilled in the art, by the use of known techniques and by observing results obtained under analogous circumstances. In determining the effective amount for a patient, a number of factors are considered by the attending diagnostician, including, but not limited to: the species of patient; its size, age, and general health; the specific disease or disorder involved; the degree of or involvement or the severity of the disease or disorder; the response of the individual patient; the particular compound administered; the mode of administration; the bioavailability characteristics of the preparation administered; the dose regimen selected; the use of concomitant medication; and other relevant circumstances.

The compounds of the present invention are generally effective over a wide dosage range. For example, dosages per day normally fall within the range of about 0.01 to about 20 mg/kg of body weight. In some instances dosage levels below the lower limit of the aforesaid range may be more than adequate, while in other cases still larger doses may be employed with acceptable side effects, and therefore the above dosage range is not intended to limit the scope of the invention in any way.

The compounds of the present invention are preferably formulated as pharmaceutical compositions administered by any route which makes the compound bioavailable, including oral and transdermal routes. Most preferably, such compositions are for oral administration. Such pharmaceutical compositions and processes for preparing same are well known in the art. (See, e.g., Remington: The Science and Practice of Pharmacy (D. B. Troy, Editor, 21st Edition, Lippincott, Williams & Wilkins, 2006).

The compounds of Formulas I and Ia, or pharmaceutically acceptable salts thereof are particularly useful in the treatment methods of the invention, but certain groups, substituents, and configurations are preferred. The following paragraphs describe such preferred groups, substituents, and configurations. It will be understood that these preferences are applicable both to the treatment methods and to the new compounds of the invention.

Thus, the compound of Formula I wherein the fused bicyclic ring is in the CIS configuration, or pharmaceutically acceptable salt thereof, is preferred. For example, one of ordinary skill in the art will appreciate that the compound of Formula Ia is in the CIS relative configuration for the centers labeled 1 and 2 as shown in Scheme A below. In addition, the compound of Formula Ia is comprised of a core that contains three chiral centers at the carbon atoms labeled 1, 2, and 3 as indicated by the arrows. The preferred relative configuration for the three chiral centers of Formula Ia is shown in Scheme A:

Scheme A

Formula Ia

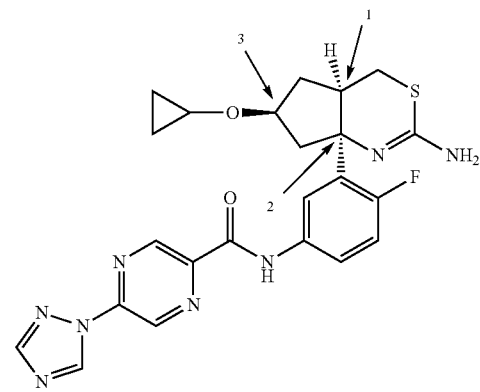

Further compounds of the present invention are:

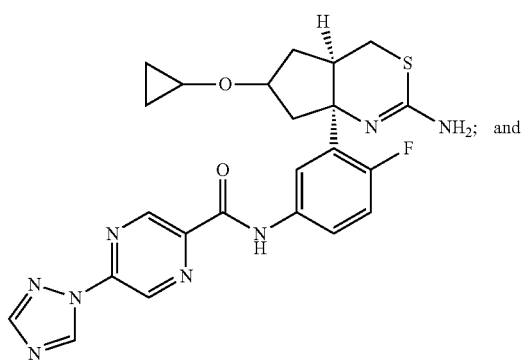

-continued

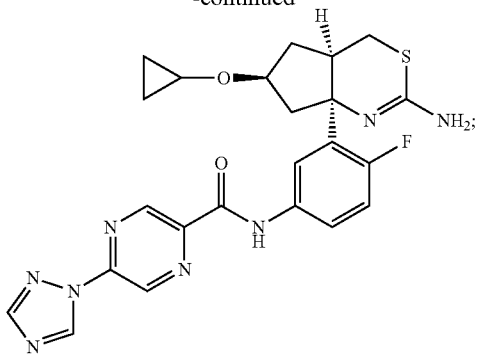

and the pharmaceutically acceptable salts thereof.

Although the present invention contemplates all individual enantiomers and diastereomers, as well as mixtures of the enantiomers of said compounds, including racemates, the compounds with the absolute configuration as set forth below are preferred:

N-[3-[(4aR,6S,7aS)-2-amino-6-(cyclopropoxy)-4a,5,6,7-tetrahydro-4H-cyclopenta[d][1,3]thiazin-7a-yl]-4-fluorophenyl]-5-(1,2,4-triazol-1-yl)pyrazine-2-carboxamide, and the pharmaceutically acceptable salts thereof.

A more preferred compound is:

N-[3-[(4aR,6S,7aS)-2-amino-6-(cyclopropoxy)-4a,5,6,7-tetrahydro-4H-cyclopenta[d][1,3]thiazin-7a-yl]-4-fluorophenyl]-5-(1,2,4-triazol-1-yl)pyrazine-2-carboxamide.

One of ordinary skill in the art will appreciate that compounds of the invention can exist in tautomeric forms, as depicted generally in Scheme B. When any reference in this application to one of the specific tautomers of the compounds of the invention is given, it is understood to encompass both tautomeric forms and all mixtures thereof.

limit the teaching of the schemes in any way. Furthermore, individual isomers, enantiomers, and diastereomers may be separated or resolved by one of ordinary skill in the art at any convenient point in the synthesis of compounds of the invention, by methods such as selective crystallization techniques or chiral chromatography (See for example, J. Jacques, et al., "Enantiomers, Racemates, and Resolutions", John Wiley and Sons, Inc., 1981, and E. L. Eliel and S. H. Wilen, "Stereochemistry of Organic Compounds", Wiley-Interscience, 1994). The designations "isomer 1" and "isomer 2" refer to the compounds that elute from chiral chromatography first and second, respectively, and if chiral chromatography is initiated early in the synthesis, the same designation is applied to subsequent intermediates and examples.

Certain abbreviations are defined as follows: "CDI" refers to 1,1'-carbonyldiimidazole; "CSF" refers to cerebrospinal fluid; "DCC" refers to 1,3-dicyclohexylcarbodiimide; "DCM" refers to dichloromethane or methylene dichloride; "DIC" refers to diisopropylcarbodiimide; "DIPEA" refers to diisopropylethylamine or N-ethyl-N-isopropyl-propan-2-amine; "ACN" refers to acetonitrile; "DMAP" refers to dimethylaminopyridine; "DMEM" refers to Dulbecco's Modified Eagle's Medium; "DMF" refers to dimethylformamide; "DMSO" refers to dimethyl sulfoxide; "EDCI" refers to 1-(3-dimethylaminopropyl)-3-ethylcarbodiimide hydrochloride; "ee" refers to enantiomeric excess; "Ex" refers to example; "F12" refers to Ham's F12 medium; "FBS" refers to Fetal Bovine Serum; "FRET" refers to fluorescence resonance energy transfer; "HATU" refers to (dimethylamino)-N,N-dimethyl(3H-[1,2,3]triazolo[4,5-b]pyridin-3-yloxy)methaniminium hexafluorophosphate; "HEK" refers to human embryonic kidney; "HOAc" refers to acetic acid; "HOAt" refers to 1-hydroxy-7-azobenzotriazole; "HOBt" refers to 1-hydroxylbenzotriazole hydrate;

Scheme B

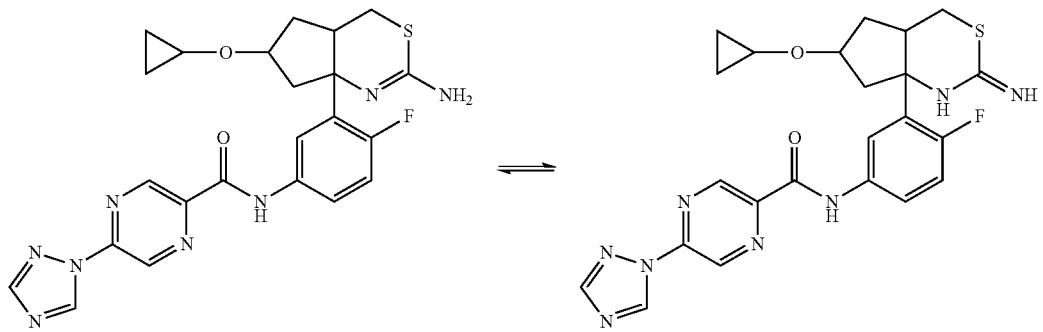

Additionally, certain intermediates described in the following schemes may contain one or more nitrogen protecting groups. The variable protecting group may be the same or different in each occurrence depending on the particular reaction conditions and the particular transformations to be performed. The protection and deprotection conditions are well known to the skilled artisan and are described in the literature (See for example "Greene's Protective Groups in Organic Synthesis", Fourth Edition, by Peter G. M. Wuts and Theodora W. Greene, John Wiley and Sons, Inc. 2007).

Certain stereochemical centers have been left unspecified and certain substituents have been eliminated in the following schemes for the sake of clarity and are not intended to "HBTU" refers to refers to 2-(1H-benzotriazole-1-yl)-1,1,3,3-tetramethyluronium hexafluorophosphate; "HPLC" refers to high-performance liquid chromatography; "IC$_{50}$" refers to the concentration of an agent that produces 50% of the maximal inhibitory response possible for that agent; "min" refers to minute or minutes; "MeOH" refers to methanol or methyl alcohol; "MTBE" refers to methyl tert-butyl ether; "OR" refers to optical rotation; "PDAPP" refers to platelet derived amyloid precursor protein; "PG" refers to protecting group; "Prep" refers to preparation; "PyBOP" refers to benzotriazol-1-yloxytripyrrolidino-phosphonium hexafluorophosphate; "PyBrop" refers to bromo-tris-pyrrolidino phosphoniumhexafluoro phosphate; "RFU" refers to relative fluorescence unit; "R$_t$" refers to retention time; "SFC" refers to supercritical fluid chromatography; and "THF" refers to tetrahydrofuran.

The compounds of the present invention, or salts thereof, may be prepared by a variety of procedures known in the art, some of which are illustrated in the Schemes, Preparations, and Examples below. One of ordinary skill in the art recognizes that the specific synthetic steps for each of the routes described may be combined in different ways, or in conjunction with steps from different schemes, to prepare compounds of the invention, or salts thereof. The products of each step in the schemes below can be recovered by conventional methods well known in the art, including extraction, evaporation, precipitation, chromatography, filtration, trituration, and crystallization. In the schemes below, all substituents unless otherwise indicated, are as previously defined. The reagents and starting materials are readily available to one of ordinary skill in the art. The following schemes, preparations, and examples further illustrate the invention.

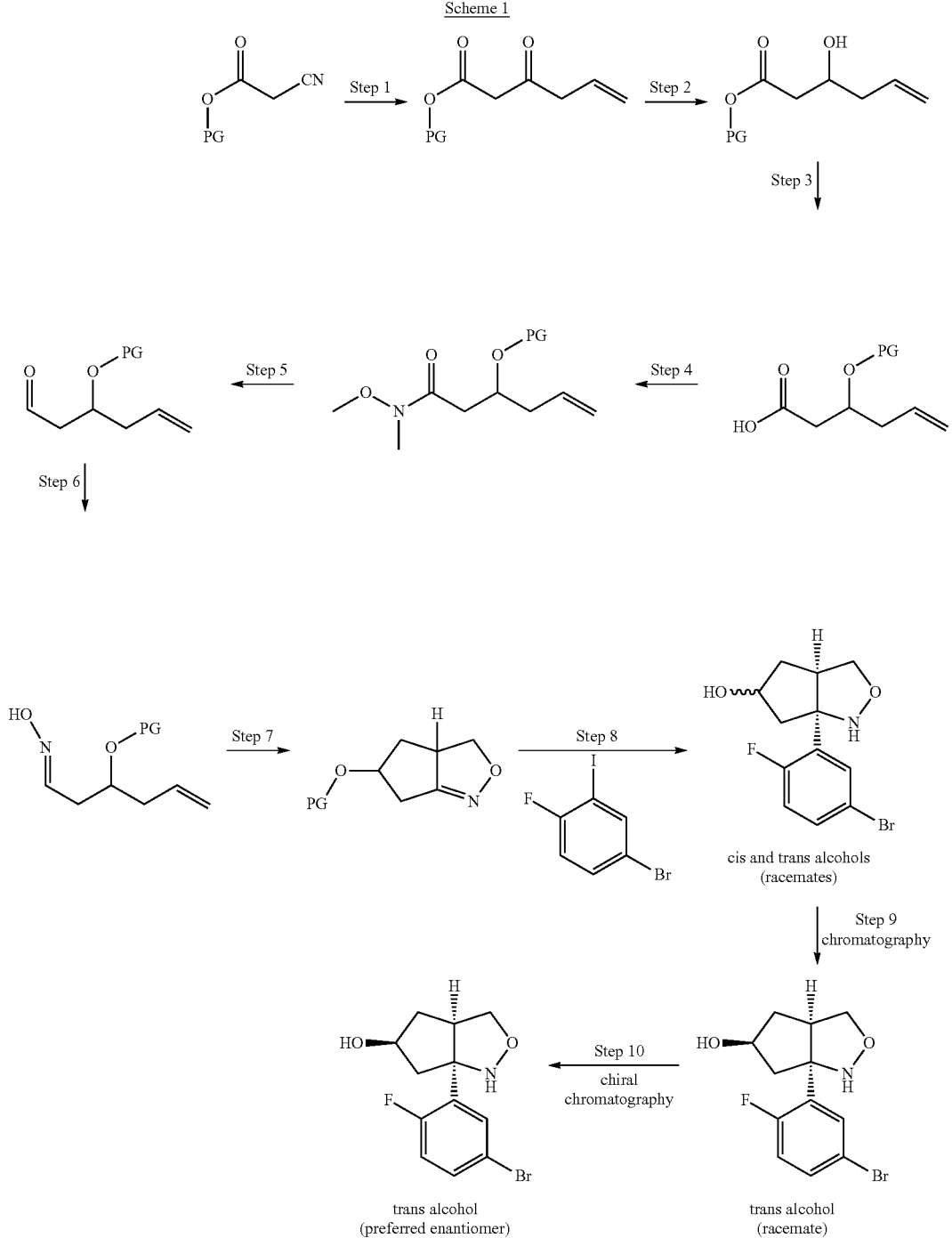

In Scheme 1, step 1, the protected methyl cyanoacetate is converted to the methyl 3-oxohex-5-enoate with 3-bromoprop-1-ene using aluminum chloride and zinc dust in a solvent such as THF to provide the corresponding ketone product. In Scheme 1, step 2, the ketone is then reduced under conditions well known in the art using a reducing agent such as sodium borohydride in a solvent such as MeOH. After an appropriate reaction time, acetone is added dropwise and the reaction is concentrated to give the hydroxy product of Scheme 1, step 2. Other common reducing agents that may be used are LiBH$_4$ or sodium triacetoxyborohydride with a catalytic amount of acid such as acetic acid. In Scheme 1, step 3, the hydroxyl group can be protected, for example, with a tert-butyl dimethyl silyl group in a solvent such as DMF using an organic base such as imidazole and tert-butyl-chloro-dimethyl-silane. "PG" is a protecting group developed for amines, esters, or hydroxy groups. Such protecting groups are well known and appreciated in the art. In addition, the ester can then be hydrolyzed under conditions well known in the art using an aqueous base such as sodium hydroxide to provide the corresponding carboxylic acid of Scheme 1, step 3. In Scheme 1, step 4, the carboxylic acid can be converted to the Weinreb amide under standard conditions using a coupling agent such as CDI in portions followed by the addition of N,O-dimethylhydroxylamine hydrochloride. In Scheme 1, step 5, the Weinreb amide is converted to the aldehyde with diisobutylaluminum hydride in a solvent such as THF at a temperature of about −30 to −60° C. Other reducing agents such as lithium aluminum hydride are well known in the art for converting the Weinreb amide to an aldehyde. In Scheme 1, step 6, the aldehyde can be converted to an oxime under conditions well known in the art with hydroxylamine hydrochloride in ethanol and an organic base such as pyridine. In Scheme 1, step 7, the corresponding oxime can be converted to the bicyclic 4,5-dihydroisoxazole in a 3+2 cyclization by several well known methods such as using an aqueous solution of sodium hypochlorite or an alternative oxidant such as N-chlorosuccinimide and in a solvent such as DCM, tert-butyl methyl ether, toluene, or xylene at a temperature of about 0° C. or with heating. In Scheme 1, step 8, the 2-fluoro, 5-bromo phenyl group can be added onto the dihydroisoxazole by generating the organometallic reagent from 4-bromo-1-fluoro-2-iodo-benzene using halogen-metal exchange with reagents such as n-butyllithium or isopropylmagnesium chloride lithium chloride complex. Dropwise addition of the organometallic reagent at a temperature of about −10 to −15° C. in a solvent such as THF with stirring followed by the addition of boron trifluoride diethyl etherate gives the alkylated product. The crude alkylated product can then be deprotected at the hydroxy using 1 M tetrabutylammonium fluoride solution in THF to provide a diastereomeric mixture of the cis and trans alcohols of Scheme 1, step 8. In Scheme 1, step 9, the diasteromeric cis/trans mixture of alcohols can be separated using standard techniques well known in the art, such as silica gel chromatography to provide the purified racemic trans alcohol (and the purified racemic cis alcohol). If desired, the racemic trans alcohol can be coverted to its corresponding HCl salt under conditions well know in the art, for example, by addition of 1.25 M HCL in 2-propanol to the racemic trans alcohol in MTBE followed by filtration to collect the resulting HCl salt. In Scheme 1, step 10, the free base of the racemic trans alcohol can be separated into its corresponding enantiomers using chiral chromatography to provide the preferred purified enantiomer.

Scheme 2

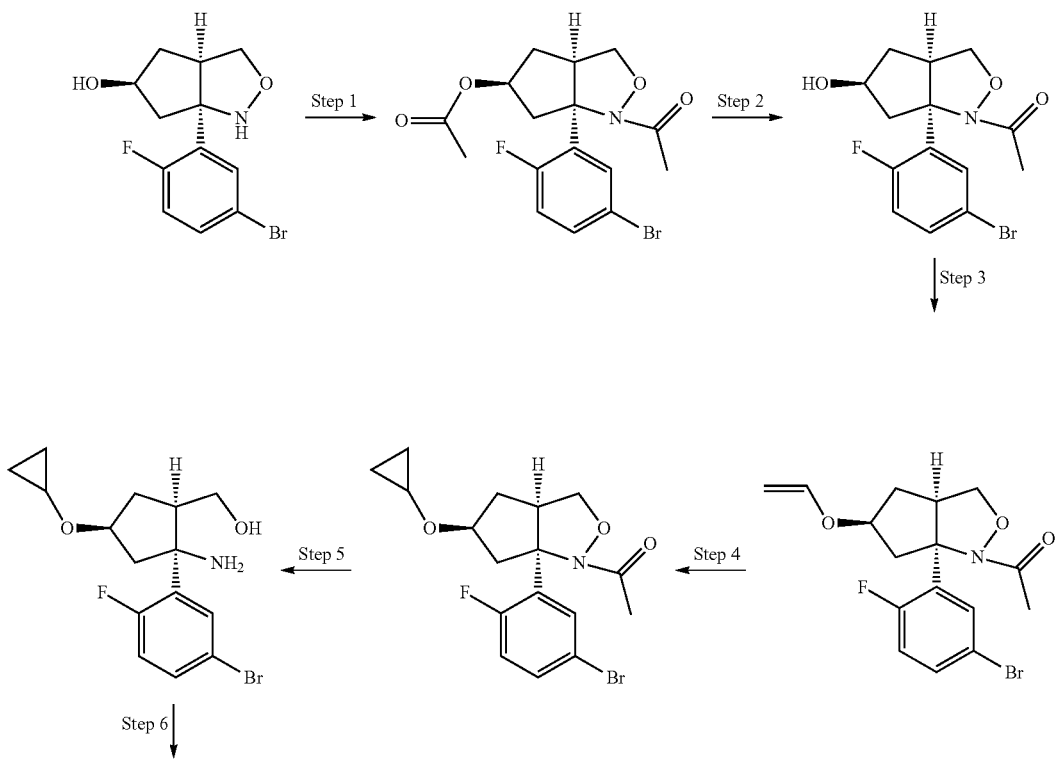

-continued

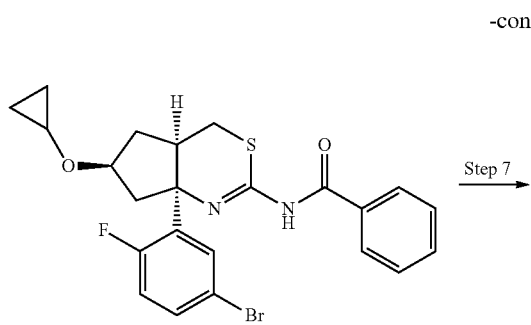

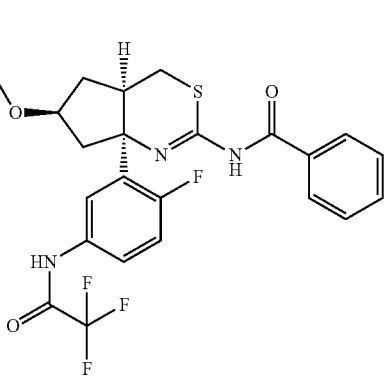

Step 7

Step 8

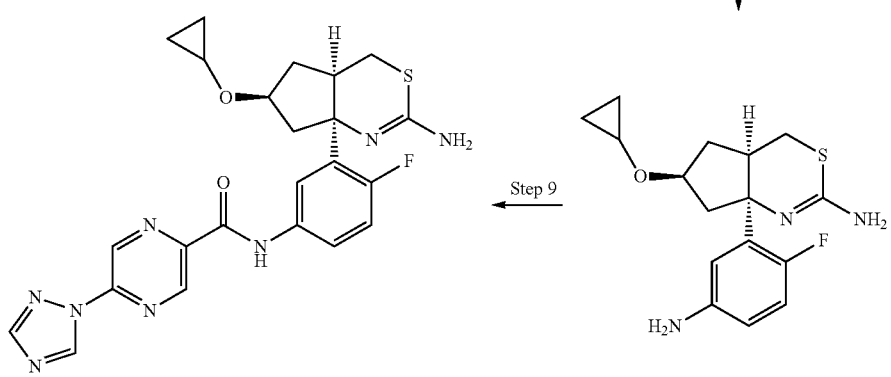

Step 9

Formula Ia

In Scheme 2, step 1, the product of Scheme 1, step 10 is protected at the tetrahydroisoxazole nitrogen and the hydroxy using DMAP, an organic base such as pyridine, and acetic anhydride in a solvent such as DCM with heating to give the diprotected product. The protected hydroxy is selectively deprotected under conditions well known in the art using aqueous sodium hydroxide in a solvent such as MeOH to give the monoprotected product of Scheme 2, step 2. In Scheme 2, step 3, a palladium coupling can be used to form the corresponding vinyl ether. For example, a catalytic amount of palladium acetate and 1,10-phenanthroline in a solvent such as DCM and ethyl vinyl ether with heating under refluxing conditions will give the product of Scheme 2, step 3. The resulting vinyl ether can then be converted to the cyclopropane under Simmons-Smith conditions with diethylzinc and chloroiodomethane in a solvent such as DCM and a temperature of about 0° C. to give the product of Scheme 2, step 4. In Scheme 2, step 5, the tetrahydroisoxazole nitrogen can be deprotected in a solvent such as THF with diisobutylaluminum hydride at a temperature of about −45° C., quenching first with MeOH and then aqueous hydrochloric acid. The tetrahydroisoxazole ring can be treated with zinc in acetic acid at a temperature of about 40° C. to form the ring opened product of Scheme 2, step 5. An alternate method to open the tetrahydroisoxazole ring uses Raney Nickel in a polar solvent such as ethanol under pressure with hydrogenation conditions. The ring opened product of Scheme 2, step 5 can then be reacted with benzoyl isothiocyanate in a solvent such as THF or DCM at a temperature of about 0° C. to room temperature followed by the addition of CDI at room temperature with heating to about 70° C. to give the thiazine product of Scheme 2, step 6. The bromide can then be converted to an amide using trifluoroacetamide, copper iodide, a diamine or related ligand such as trans, racemic-N1,N2-dimethylcyclohexane-1,2-diamine, an inorganic base such as potassium carbonate, and sodium iodide with heating to about 100-110° C. to give the amide product of Scheme 2, step 7. The amide and the thiazine amine can then be deprotected under conditions well known in the art using an aqueous base such as sodium hydroxide in a solvent such as MeOH to give the deprotected aniline of Scheme 2, step 8. The deprotected aniline can be then be coupled with a heteroaromatic carboxylic acid utilizing coupling conditions well known in the art. One skilled in the art will recognize that there are a number of methods and reagents for amide formation resulting from the reaction of carboxylic acids and amines. For example, in Scheme 2, step 9, the reaction of the appropriate aniline with an appropriate carboxylic acid in the presence of a coupling reagent will provide the amide of Formula Ia. Coupling reagents include HATU or carbodiimides such as DCC, DIC, EDCI, and aromatic oximes such as HOBt and HOAt. Additionally, uronium or phosphonium salts of non-nucleophilic anions such as HBTU, PyBOP, and PyBrOP can be used in place of the more traditional coupling reagents. Organic bases such as triethylamine, diisopropylethylamine, or DMAP may be used to enhance the reaction. Alternatively, the aniline can be acylated using substituted benzoyl chlorides in the presence of a base such as triethylamine or pyridine to provide the compound of Formula Ia.

A pharmaceutically acceptable salt of the compounds of the invention, such as a hydrochloride salt, can be formed, for example, by reaction of an appropriate free base of Formula I or Ia, an appropriate pharmaceutically acceptable acid such as hydrochloric acid in a suitable solvent such as diethyl ether under standard conditions well known in the art. Additionally, the formation of such salts can occur simultaneously upon deprotection of a nitrogen protecting group. The formation of such salts is well known and appreciated in the art. See, for example, Gould, P. L., "Salt selection for basic drugs," *International Journal of Pharmaceutics*, 33: 201-217 (1986); Bastin, R. J., et al. "Salt Selection and Optimization Procedures for Pharmaceutical New Chemical Entities," *Organic Process Research and Development*, 4: 427-435 (2000); and Berge, S. M., et al., "Pharmaceutical Salts," *Journal of Pharmaceutical Sciences*, 66: 1-19, (1977).

The following preparations and examples further illustrate the invention.

PREPARATION 1

Methyl 3-oxohex-5-enoate

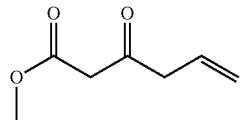

Scheme 1, step 1: Charge methyl cyanoacetate (2700 g, 27.2 mol) and THF (32 L) into a 72 L round bottom flask equipped with a mechanical stirrer, addition funnel and temperature probe under a nitrogen atmosphere. Cool to 5° C. and add aluminum (III) chloride (363 g, 2.72 mol) and zinc dust (2320 g, 35.42 mol) in portions maintaining internal temperature below 28° C. Stir under nitrogen for 25 minutes and add 3-bromoprop-1-ene (3960 g, 3510 mL, 32.70 mol) by addition funnel at a rate such that the internal temperature of the reaction mixture remains below 21° C. Stir at ambient temperature overnight. Filter through diatomaceous earth rinsing with THF (4 L) and evaporate the filtrate under reduced pressure. Dissolve the residue in MTBE (8 L) and add to a stirred solution of 1 N aqueous hydrochloric acid (12 L). Cool to 0° C. and add 6 N aqueous hydrochloric acid (3 L) followed by the addition of concentrated hydrochloric acid (2.3 L) maintaining the internal temperature below 40° C. until pH 1-2 is obtained. Separate the organic phase and wash with brine (6 L), dry over sodium sulfate, and filter through a plug of silica gel, eluting with MTBE (8 L). Concentrate the filtrate under reduced pressure to obtain the title compound as a dark oil (4500 g, 99%, 74% purity by GCMS). EI MS m/z 142.0 [M+H]$^+$.

PREPARATION 2

Methyl 3-hydroxyhex-5-enoate

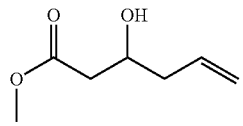

Scheme 1, step 2: Charge a solution of methyl 3-oxohex-5-enoate (4271 g, 30.05 mol) in MeOH (30 L) into a 72 L round bottom flask equipped with mechanical stirrer and temperature probe under a nitrogen atmosphere. Cool to an internal temperature of 5° C. then add sodium borohydride (1137 g, 30.05 mol) in portions maintaining the internal temperature below 16° C. Stir at ambient temperature overnight. Add acetone (325 mL) dropwise and concentrate the resulting mixture under reduced pressure. Partition the residue between MTBE (20 L), brine (7 L) and water (7 L). Separate the layers and wash with brine (1×10 L), dry over sodium sulfate, filter, and evaporate to dryness under reduced pressure to obtain the title compound (3230 g, 75%, 74% purity by GC/MS) as a dark oil. EI MS m/z 144.0 [M+H]$^+$.

PREPARATION 3

Methyl 3-{[tert-butyl(dimethyl)silyl]oxy}hex-5-enoate

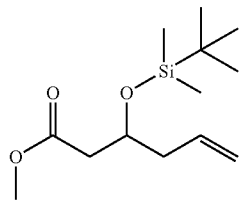 [SMILES: C=CCC(CC(=O)OC)O[Si](C)(C)C(C)(C)C]

Scheme 1, step 3 (protection of alcohol): Dissolve methyl 3-hydroxyhex-5-enoate (24.5 kg, 170.1 mol, 1.0 eq) in DMF (245 L) and cool to 0° C. Add imidazole (23.1 kg, 340.2 mol) in one portion followed by tert-butyl-chloro-dimethyl-silane (51.4 kg, 340.2 mol) in portions over 30 minutes maintaining internal temperature between 0~7° C. Stir the reaction mixture at this temperature for 20 minutes and then heat to 40° C. overnight or until the reaction is complete. Then add MTBE (150 L) and water (120 L) with stirring and separate the layers. Wash the organic layer with water (100 L) and brine (60 L), dry over anhydrous sodium sulfate, and concentrate to give the title compound (40 kg, 91%) as a dark brown oil. ES/MS: m/z 259.1 [M+H]$^+$.

PREPARATION 4

3-{[tert-Butyl(dimethyl)silyl]oxy}hex-5-enoic acid

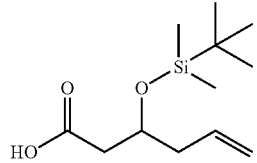 [SMILES: C=CCC(CC(=O)O)O[Si](C)(C)C(C)(C)C]

Scheme 1, step 3 (deprotection of carboxylic acid): Dissolve methyl 3-{[tert-butyl(dimethyl)silyl]oxy}hex-5-enoate (40 kg, 154.8 mol) in methanol (160 L) and cool to 3-5° C. Add a solution of sodium hydroxide (18.6 kg, 464.3 mol, 3.0 eq) in water (225 L) dropwise over 2 hours keeping the internal temperature below 15° C. Heat the reaction to 60° C. and stir for 4 hours. Repeat this procedure on the same scale and combine the two reaction mixtures. Remove methanol under vacuum at 55° C. Wash the resulting aqueous solution with DCM (60 L) and cool the aqueous layer to 3-5° C. Add concentrated HCl until pH 1-2 is reached while maintaining the internal temperature below 20° C. Extract the mixture with DCM (70 L). Separate the layers and wash the organic layer with brine (50%, 60 L), dry over anhydrous sodium sulfate and concentrate to give the title compound (48 kg, 63%) as a dark brown oil. EI MS: m/z 203.0 [M-allyl].

PREPARATION 5

3-{[tert-Butyl(dimethyl)silyl]oxy}-N-methoxy-N-methylhex-5-enamide

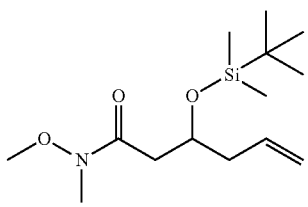 [SMILES: C=CCC(CC(=O)N(C)OC)O[Si](C)(C)C(C)(C)C]

Scheme 1, step 4: Stir a solution of 3-{[tert-butyl(dimethyl)silyl]oxy}hex-5-enoic acid (6.3 kg, 25.8 mol) in DCM (25 L) and cool to 5-10° C. under nitrogen. Add CDI (4.6 kg, 28.4 mol) in portions while maintaining the internal temperature below 10° C. Stir at this temperature for 2 hours. Add N,O-dimethylhydroxylamine hydrochloride (4.05 kg, 41.3 mol) in one portion and heat the reaction mixture to 40° C. for 24 hours. Cool the reaction mixture to ambient temperature and pour into 1 N hydrochloric acid (30 L) with stirring. Wash the organic phase with saturated aqueous sodium bicarbonate (20 L), brine (10 L), and dry over anhydrous sodium sulfate. Repeat the reaction twice, combine the crude DCM solutions, and concentrate under vacuum to give a residue. Vacuum distill the mixture (65-95° C., 2-5 Pa) to give the title compound (9.02 kg, 40%) as a yellow oil. EI MS m/z 287 [M+H]$^+$.

PREPARATION 6

3-{[tert-Butyl(dimethyl)silyl]oxy}hex-5-enal

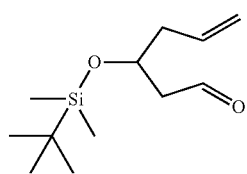

Scheme 1, step 5: Charge a 50 L round bottom flask with diisobutylaiuminum hydride (1 M in hexanes, 18.3 L), stir, and cool to an internal temperature of −50~−60° c. using a dry ice-acetone bath. Add a solution of 3-[tert-butyl(dimethyl)silyl]oxy-N-methoxy-N-methyl-hex-5-enamide (5.00 kg, 17.39 mol) in THF (15 L) over 1.5-2 hours while maintaining the internal temperature below −50° C. and stir the reaction solution at −30~−50° C. for 2 hours. Ensuring that internal temperature does not exceed 20° C., slowly add water (300 mL) followed by dilute hydrochloric acid (3 M, 1 L). Pour this mixture into a cooled solution of dilute hydrochloric acid (3 M, 36 L) ensuring that the internal temperature does not exceed 20° C. Separate the organic phase and wash with water (2×8 L) and brine (5 L), dry over anhydrous sodium sulfate, and concentrate to give the title compound (2.90 kg, 73%) as brown oil. EI MS m/z 187.2 [M-allyl].

PREPARATION 7

3-{[tert-Butyl(dimethyl)silyl]oxy}-N-hydroxyhex-5-en-1-imine

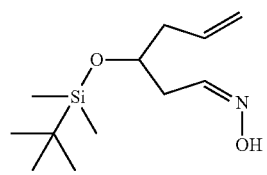 [SMILES: C=CCC(C/C=N\O)O[Si](C)(C)C(C)(C)C]

Scheme 1, step 6: Stir a suspension of pyridine (1.61 kg, 20.36 mol) and hydroxylamine hydrochloride (1.23 kg, 17.64 mol) in ethanol (9.3 L) at 15° C. for 30 minutes. Add a solution of 3-[tert-butyl(dimethyl)silyl]oxyhex-5-enal (3.10 kg, 13.57 mol) in ethanol (3.1 L) and stir at 15-20° C. for 2 hours. Remove ethanol under reduced pressure and add MTBE (4 L) and brine (4 L) to the residue. Separate the resulting suspension and wash the organic phase with 0.5 N hydrochloric acid (2×3 L), then brine (3 L). Dry over anhydrous sodium sulfate and concentrate to give the title compound (mixture of E/Z isomers 3.00 kg, 91%) as a brown oil. EI MS m/z 202.0 [M-allyl].

PREPARATION 8

5-{[tert-Butyl(dimethyl)silyl]oxy}-3a,4,5,6-tetrahydro-3H-cyclopenta[c][1,2]oxazole

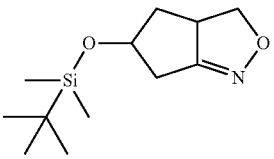 [SMILES: CC(C)(C)[Si](C)(C)OC1CC2=NOCC2C1]

Scheme 1, step 7: In a 50 L round bottom flask dissolve 3-{[tert-butyl(dimethyl)silyl]oxy}-N-hydroxyhex-5-en-1-imine (2.00 kg, 8.22 mol) in DCM (20 L), stir and cool to −7° C. with an ice-ethanol bath. Add a solution of 7-8 wt % strength aqueous sodium hypochlorite (15.5 L) via additional funnel while maintaining the internal temperature below 0° C. Stir at 0° C. for 30 minutes. Separate the layers and wash the organic phase with saturated aqueous sodium sulfite (2×10 L) then brine (5 L). Dry over anhydrous sodium sulfate, concentrate, and purify by silica gel flash column chromatography eluting with a gradient from 2.5% to 9% ethyl acetate in isohexane to give the title compound as yellow oil (1.01 kg, 51%) and as a mixture of diastereomers. ES/MS: m/z 242 [M+H]$^+$.

PREPARATION 9 rel-(3aR,5S,6aS)-6a-(5-Bromo-2-fluorophenyl)hexahydro-1H-cyclopenta[c][1,2]oxazol-5-ol hydrochloride (Trans Alcohol)

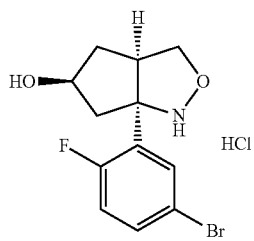 [SMILES: O[C@H]1C[C@H]2CON[C@@]2(c2cc(Br)ccc2F)C1 ; Cl]

PREPARATION 10 rel-(3aR,5R,6aS)-6a-(5-Bromo-2-fluorophenyl)hexahydro-1H-cyclopenta[c][1,2]oxazol-5-ol hydrochloride (Cis Alcohol)

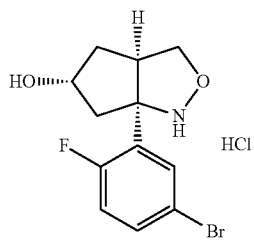 [SMILES: O[C@@H]1C[C@H]2CON[C@@]2(c2cc(Br)ccc2F)C1 ; Cl]

Scheme 1, steps 8 and 9 (for preparations 9 and 10): Stir a solution of 4-bromo-1-fluoro-2-iodo-benzene (149.6 g, 497.1 mmol) in anhydrous THF (600 mL) at −10° C. under a nitrogen atmosphere and add dropwise a 1.3 M solution of isopropylmagnesium chloride lithium chloride complex in THF (382 mL, 497 mmol). Stir at −15° C. for 1 hour. Add a solution of 5-{[tert-butyl(dimethyl)silyl]oxy}-3a,4,5,6-tetrahydro-3H-cyclopenta[c][1,2]oxazole (60 g, 248.54 mmol) in anhydrous toluene (300 mL) maintaining the internal temperature below −5° C. After 20 minutes add boron trifluoride diethyletherate (63 mL, 497.1 mmol) and stir between 0° C. to 10° C. for 1 hour. Add saturated aqueous ammonium chloride solution (500 mL) and partition between water (200 mL) and ethyl acetate (300 mL). Wash the organic layer with brine solution (500 mL), dry over magnesium sulfate, filter, and concentrate under reduced pressure to give a dark orange oil. Dissolve the residue in THF (240 mL), stir, and cool in an ice/water bath. Add 1 M tetrabutylammonium fluoride solution in THF (546 mL) and allow to warm to ambient temperature. Stir until LCMS indicates complete desilylation and partition between water (500 mL) and ethyl acetate (500 mL) and separate the phases. Extract the aqueous layer with ethyl acetate (500 mL), wash the combined organic extracts with water (500 mL) and brine (500 mL), dry over magnesium sulfate, filter, and concentrate under reduced pressure to give a mixture of cis/trans diastereomers. Separate the cis/trans diastereomers by silica gel flash chromatography eluting with 30%-70% ethyl acetate in isohexane to obtain separate cis and trans diastereomers (see Scheme 1, step 9). Dissolve rel-(3aR,5S,6aS)-6a-(5-bromo-2-fluorophenyl)hexahydro-1H-cyclopenta[c][1,2]oxazol-5-ol (22.19 g, 73 mmol, trans alcohol) in MTBE (200 mL) and add 1.25 M hydrochloric acid in 2-propanol (60 mL, 75 mmol) at 45° C. Stir for 10 minutes and collect the resulting white solid by filtration, washing with MTBE (2×50 mL). Dry under nitrogen to obtain the title compound of Preparation 9 (20.88 g, 25%) as a white powder. $R_t$ 0.99 min, ES/MS: m/e ($^{79}Br/^{81}Br$) 302.0/304.0 [M+H].

Partition rel-(3aR,5R,6aS)-6a-(5-bromo-2-fluorophenyl)hexahydro-1H-cyclopenta[c][1,2]oxazol-5-ol (67.7 g, contaminated with tetrabutylammonium fluoride, (cis alcohol) between MTBE (300 mL) and water (300 mL) and wash the organic layer with saturated aqueous ammonium chloride solution (300 mL), water (300 mL) and 2 N aqueous hydrochloric acid (3×200 mL). Add 50% aqueous sodium hydroxide until the pH reaches pH 10 and extract with MTBE (3×150 mL). Wash the combined organic extracts with water (300 mL) and brine (300 mL). Treat the organic layer with 1.25 M hydrochloric acid in 2-propanol (180 mL, 225 mmol) and stir for 10 minutes. Evaporate the solution to dryness and triturate the residue in ethyl acetate (200 mL), filter and air dry to give the title compound of Preparation 10 as a white powder (16.71 g, 20%). ES/MS: m/e ($^{79}Br/^{81}Br$) 301.8/303.8 [M+H], $R_t$ 0.85 min, analytical reverse phase conditions: Phenomenex Gemini-NX C18 column of 50 mm length, 2.1 mm internal diameter and 3 µm particle size. The mobile phase: Al=water with 0.1% formic acid/B1=ACN with 0.1% formic acid, temperature of 50° C., a flow rate of 1.2 mL/min, with a gradient elution from 5% to 95% (B1) over 1.5 min followed by a 0.5 min hold at 95% (B1).

PREPARATION 11

(3aR,5S,6aS)-6a-(5-Bromo-2-fluorophenyl)hexahydro-1H-cyclopenta[c][1,2]oxazol-5-ol

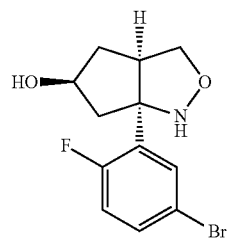

Scheme 1, step 10: Suspend rel-(3aR,5S,6aS)-6a-(5-bromo-2-fluorophenyl)hexahydro-1H-cyclopenta[c][1,2]oxazol-5-ol hydrochloride (200.0 g, 66 mmol, trans alcohol) in MTBE (6 L), and add water (4 L) and 2 N aqueous sodium hydroxide (400 mL). Stir for 20 minutes, separate the layers, and extract the aqueous layer with MTBE (2×500 mL). Combine the organic extracts and wash with water (2 L) and brine. Dry over sodium sulfate, filter, and concentrate under vacuum to give the racemic freebase (182.5 g). Separate the enantiomers by chiral SFC (Supercritical Fluid Chromatography) (Column: Chiralpak AD-H (5µ), 50×250 mm; eluent: 22% EtOH (0.2% diethylmethylamine) in $CO_2$; flow: 350 g/min at UV 220 nm). The first eluting enantiomer is the title compound (83.94 g, 47%). OR $[\alpha]_D^{20}$=+73° (C=0.247, DCM), ES/MS: m/e ($^{79}Br/^{81}Br$) 302.0/304.0 [M+H], $R_t$ 0.88 min.

PREPARATION 12

5-(1H-1,2,4-Triazol-1-yl)pyrazine-2-carboxylic acid

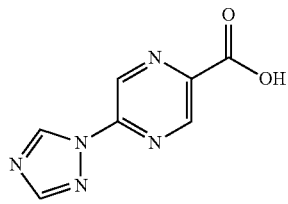 [SMILES: O=C(O)c1cnc(-n2cncn2)cn1]

Stir a mixture of methyl 5-chloropyrazine-2-carboxylate (124 g, 718.55 mmol), 1H-1,2,4-triazole (198.5 g, 2874.2 mmol) and potassium carbonate (297.92 g, 2155.6 mmol) in DMF (1000 mL) at 100° C. for 15 hours. Cool to ambient temperature and pour into water (2 L). Adjust to pH 2-3 using concentrated aqueous hydrochloric acid (about 500 mL) and stir for 30 minutes. Collect the resulting solid by filtration and wash with water. Add water (500 mL) and ethanol (500 mL) and heat to 50-60° C. for 4 hours and cool to ambient temperature. Collect the solids by filtration and dry under vacuum at 40° C. to give the title compound as a white solid. ES/MS: m/z 190.0 (M−H).

PREPARATION 13

(3aR,5S,6aS)-1-Acetyl-6a-(5-bromo-2-fluorophenyl)hexahydro-1H-cyclopenta[c][1,2]oxazol-5-yl acetate

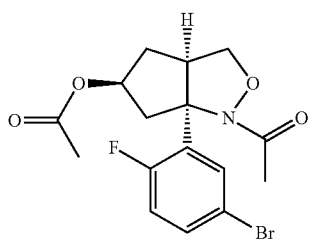 [SMILES: CC(=O)O[C@H]1C[C@H]2CON(C(C)=O)[C@@]2(c2cc(Br)ccc2F)C1]

Scheme 2, step 1: Stir a solution of (3aR,5S,6aS)-6a-(5-bromo-2-fluorophenyl)hexahydro-1H-cyclopenta[c][1,2]oxazol-5-ol (36.16 g, 119.7 mmol), DMAP (3.69 g, 29.9 mmol) and pyridine (38.7 mL, 478.7 mmol) in DCM (362 mL) under nitrogen and add acetic anhydride (45.3 mL, 478.7 mmol) dropwise. Heat the reaction mixture to reflux for 18 hours. If incomplete conversion is observed by LCMS, charge further acetic anhydride and continue heating. Cool to ambient temperature and slowly add saturated aqueous sodium bicarbonate (650 mL). Extract the aqueous layer with DCM (2×200 mL), dry the combined organic extract over sodium sulfate, filter, and concentrate under vacuum. Purify the residue by silica gel flash chromatography, eluting with 0% to 50% ethyl acetate in isohexane to give the title compound as a white solid (57.7 g, contaminated with acetic acid). Carry this material on without further purification. ES/MS: m/e ($^{79}$Br/$^{81}$Br) 386.0/388.0 [M+H].

PREPARATION 14

1-[(3aR,5S,6aS)-6a-(5-Bromo-2-fluoro-phenyl)-5-hydroxy-3a,4,5,6-tetrahydro-3H-cyclopenta[c]isoxazol-1-yl]ethanone

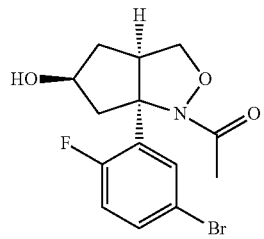 [SMILES: CC(=O)N1OC[C@@H]2C[C@H](O)C[C@@]21c1cc(Br)ccc1F]

Scheme 2, step 2: Dissolve (3aR,5S,6aS)-1-acetyl-6a-(5-bromo-2-fluorophenyl)hexahydro-1H-cyclopenta[c][1,2]oxazol-5-yl acetate (57.7 g, 149.4 mmol) in methanol (923 mL) and add 2 N aqueous sodium hydroxide (150 mL, 298.9 mmol) and stir at ambient temperature for 2 hours. Remove most of the organic solvent under reduced pressure then dilute with ethyl acetate (300 mL) and water (300 mL). Separate the layers, extract the aqueous layer with ethyl acetate (2×200 mL) and wash the combined organic extracts with brine, dry over sodium sulfate, filter, and concentrate under vacuum to give the title compound as a white solid (39.45 g, 77%). ES/MS: m/e ($^{79}$Br/$^{81}$Br) 344.0/346.0 [M+H].

PREPARATION 15

1-[(3aR,5S,6a5)-6a-(5-Bromo-2-fluoro-phenyl)-5-vinyloxy-3a,4,5,6-tetrahydro-3H-cyclopenta[c]isoxazol-1-yl]ethanone

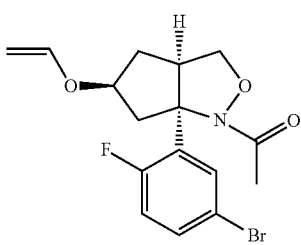 [SMILES: C=CO[C@H]1C[C@H]2CON(C(C)=O)[C@@]2(c2cc(Br)ccc2F)C1]

Scheme 2, step 3: Dissolve palladium (II) acetate (2.50 g, 11.16 mmol) and 1,10-phenanthroline (2.28 g, 12.28 mmol) in DCM (192 mL) under nitrogen and stir for 10 minutes. Add ethyl vinyl ether (855 mL) and degas the mixture with vacuum/nitrogen cycles. Stir for 15 minutes at ambient temperature and add a solution of 1-[(3aR,5S,6aS)-6a-(5-bromo-2-fluoro-phenyl)-5-hydroxy-3a,4,5,6-tetrahydro-3H-cyclopenta[c]isoxazol-1-yl]ethanone (38.41 g, 111.6 mmol) in anhydrous DCM (461 mL) via cannula and degas the resulting mixture again. Heat to reflux under nitrogen for 18 hours. If the reaction does not reach completion, further charges of palladium (II) acetate and 1,10-phenanthroline should be added to drive the reaction to completion. Cool to ambient temperature, dilute with water (100 mL) and DCM (50 mL), and stir for 5 minutes. Filter through diatomaceous earth and separate the layers. Extract the aqueous layer with DCM (3×50 mL) and wash the combined organic extracts with water (150 mL) then brine (100 mL). Dry the solution over sodium sulfate, filter, and concentrate under vacuum to give a residue. Purify the residue by silica gel flash chromatography, eluting with 0% to 40% ethyl acetate in isohexane to give the title compound as a pale yellow oil (32.52 g, 79%). ES/MS: m/e ($^{79}$Br/$^{81}$Br) 370.0/372.0 [M+H].

PREPARATION 16

1-[(3aR,5S,6aS)-6a-(5-Bromo-2-fluoro-phenyl)-5-(cyclopropoxy)-3a,4,5,6-tetrahydro-3H-cyclopenta[c]isoxazol-1-yl]ethanone

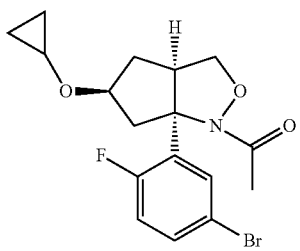 [SMILES: CC(=O)N1OC[C@@H]2C[C@H](OC3CC3)C[C@@]21c1cc(Br)ccc1F]

Scheme 2, step 4: Cool anhydrous DCM (333 mL) to 0° C. under nitrogen and add 1 M diethylzinc in hexanes (198.0 mL, 198 mmol) via cannula. Add chloroiodomethane (33.45 mL, 449.9 mmol) dropwise and stir at 0° C. for 10 minutes. Add a solution of 1-[(3aR,5S,6aS)-6a-(5-bromo-2-fluoro-phenyl)-5-vinyloxy-3a,4,5,6-tetrahydro-3H-cyclopenta[c]isoxazol-1-yl]ethanone (33.31 g, 89.98 mmol) in anhydrous DCM (200 mL) dropwise and stir at 0° C. for 1 hour. Slowly add saturated aqueous ammonium chloride (500 mL) at 0° C. and filter the biphasic mixture through diatomaceous earth. Separate the layers, extract the aqueous layer with DCM (2×200 mL) and wash the combined organic extracts with water (250 mL). Dry over sodium sulfate, filter, and concentrate under vacuum to give a residue. Purify the residue by silica gel flash chromatography, eluting with 0% to 30% MTBE in isohexane to give the title compound as a colorless oil (27.67 g, 80%). ES/MS: m/e ($^{79}$Br/$^{81}$Br) 384.0/386.0 [M+H].

PREPARATION 17

(3aR,5S,6aS)-6a-(5-Bromo-2-fluoro-phenyl)-5-(cyclopropoxy)-1,3,3a,4,5,6-hexahydrocyclopenta[c]isoxazole

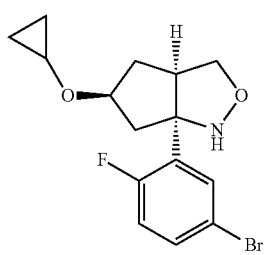 [SMILES: Fc1ccc(Br)cc1[C@]12C[C@@H](OC3CC3)C[C@H]1CON2]

Scheme 2, step 5 (deprotection): Dissolve 1-[(3aR,5S,6aS)-6a-(5-bromo-2-fluoro-phenyl)-5-(cyclopropoxy)-3a,4,5,6-tetrahydro-3H-cyclopenta[c]isoxazol-1-yl]ethanone (27.67 g, 72 mmol) in anhydrous THF (332 mL) and cool to −45° C. Add 1 M diisobutylaluminum hydride in hexanes (108 mL, 108 mmol) slowly, maintaining internal temperature below −40° C. and stir at −40° C. to −45° C. for 1 hour. Add cold methanol (−45° C., 9 mL) to the cold reaction mixture and remove the cooling bath. Slowly add 2 N aqueous hydrochloric acid (36 mL, 72 mmol) maintaining the internal temperature below 5° C. After the mixture reaches ambient temperature add water (150 mL) and ethyl acetate (150 mL) and stir for 5 minutes, separate the layers, and extract with ethyl acetate (2×100 mL). Dry the combined organic extracts over sodium sulfate, filter, and concentrate under vacuum to give the title compound as a pale yellow oil (23.16 g, 94%). ES/MS: m/e ($^{79}$Br/$^{81}$Br) 342.0/344.0 [M+H].

PREPARATION 18

[(1R,2S,4S)-2-Amino-2-(5-bromo-2-fluorophenyl)-4-(cyclopropyloxy)cyclopentyl]methanol

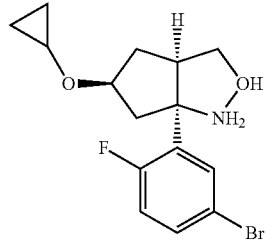 [SMILES: Fc1ccc(Br)cc1[C@]12C[C@@H](OC3CC3)C[C@H]1CON2]

Scheme 2, step 5 (ring opening): Suspend (3aR,5S,6aS)-6a-(5-bromo-2-fluoro-phenyl)-5-(cyclopropoxy)-1,3,3a,4,5,6-hexahydrocyclopenta[c]isoxazole (23.16 g, 67.7 mmol) and zinc powder (26.55 g, 406.1 mmol) in acetic acid (301 mL) and stir at 40° C. under nitrogen for 3 hours. Cool to ambient temperature and dilute with ethyl acetate (100 mL). Filter through diatomaceous earth, washing with ethyl acetate and concentrate the filtrate under vacuum. Dilute with water (200 mL), ethyl acetate (250 mL) and 27% aqueous citric acid (128 mL). Adjust the pH to pH 9-10 with saturated aqueous sodium carbonate (about 550 mL) and separate the layers. Extract the aqueous layer with ethyl acetate (2×100 mL) and dry the combined organic extracts over sodium sulfate, filter, and concentrate under vacuum to give the title compound as a pale yellow oil (24.51 g, contaminated with acetic acid). Use the product without further purification. ES/MS: m/e ($^{79}$Br/$^{81}$Br) 344.0/346.0 (M+H).

PREPARATION 19

N-[(4aR,6S,7aS)-7a-(5-Bromo-2-fluoro-phenyl)-6-(cyclopropoxy)-4a,5,6,7-tetrahydro-4H-cyclopenta[d][1,3]thiazin-2-yl]benzamide

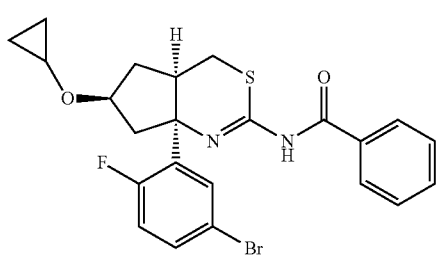 [SMILES: O=C(NC1=N[C@@]2(c3cc(Br)ccc3F)C[C@@H](OC3CC3)C[C@H]2CS1)c1ccccc1]

Scheme 2, step 6: Add benzoyl isothiocyanate (5.13 g, 31.5 mmol) dropwise to a solution of [(1R,2S,4S)-2-amino-2-(5-bromo-2-fluorophenyl)-4-(cyclopropyloxy)cyclopentyl]methanol (10.31 g, 29.95 mmol) in anhydrous THF (103 mL) at 0° C. Stir for 15 minutes then warm to ambient temperature for 1 hour. Add 1,1'-carbonyldiimidazole (5.95 g, 35.9 mmol) and stir at ambient temperature for 2 hours and 70° C. for 6 hours. Cool to ambient temperature and dilute with ethyl acetate (150 mL) and water (150 mL). Adjust the pH to pH=3.5-4.0 using 27% aqueous citric acid (45 mL) and separate the layers. Extract the aqueous layer with ethyl acetate (2×100 mL) and wash combined organic extracts with water (200 mL) and brine (100 mL). Dry over sodium sulfate, filter, and concentrate under vacuum to give a residue. Purify the residue by silica gel flash chromatography, eluting with 0% to 40% MTBE in isohexane to give the title compound as a white foam (13.89 g, 95%). ES/MS: m/e ($^{79}$Br/$^{81}$Br) 489.0/491.0 [M+H].

PREPARATION 20

N-[(4aR,6S,7aS)-6-(Cyclopropoxy)-7a-[2-fluoro-5-[(2,2,2-trifluoroacetyl)amino]phenyl]-4a,5,6,7-tetrahydro-4H-cyclopenta[d][1,3]thiazin-2-yl]benzamide

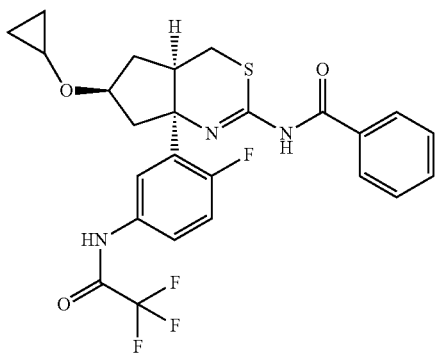 [SMILES: O=C(NC1=N[C@@]2(c3cc(NC(=O)C(F)(F)F)ccc3F)C[C@@H](OC3CC3)C[C@H]2CS1)c1ccccc1]

Scheme 2, step 7: Add a degassed solution of N-[(4aR,6S,7aS)-7a-(5-bromo-2-fluoro-phenyl)-6-(cyclopropoxy)-4a,5,6,7-tetrahydro-4H-cyclopenta[d][1,3]thiazin-2-yl]benzamide (13.89 g, 28.4 mmol) in anhydrous 1,4-dioxane (167 mL) to 4A molecular sieves (2.22 g), 2,2,2-trifluoroacetamide (5.62 g, 48.2 mmol), potassium carbonate (7.06 g, 51.1 mmol), (trans, racemic)-N1,N2-dimethylcyclohexane-1,2-diamine (1.27 g, 8.5 mmol), copper (I) iodide (1.08 g, 5.67 mmol), and sodium iodide (7.23 g, 48.25 mmol) and degas the resulting mixture. Stir the mixture and heat to 100-110° C. under nitrogen for 22 hours. If full conversion is not achieved, further 2,2,2-trifluoroacetamide, potassium carbonate (trans, racemic)-N1,N2-dimethylcyclohexane-1,2-diamine, and copper (I) iodide can be added and heating continued. Cool the reaction mixture to ambient temperature and dilute the reaction mixture with ethyl acetate (100 mL) and water (100 mL), then filter through diatomaceous earth. Separate the layers and wash the organic layer with water (3×100 mL) and brine (100 mL). Dry the solution over sodium sulfate, filter, and concentrate under vacuum to give a residue. Purify the residue by silica gel chromatography, eluting with 5% to 35% ethyl acetate in isohexane to give the title compound as a white solid (10.03 g, 68%). ES/MS: m/z 522.0 (M+H).

PREPARATION 21

(4aR,6S,7aS)-7a-(5-Amino-2-fluorophenyl)-6-(cyclopropyloxy)-4,4a,5,6,7,7a-hexahydrocyclopenta[d][1,3]thiazin-2-amine

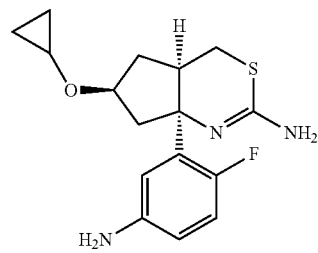 [SMILES: NC1=N[C@@]2(c3cc(N)ccc3F)C[C@@H](OC3CC3)C[C@H]2CS1]

Scheme 2, step 8: Dissolve N-[(4aR,6S,7aS)-6-(cyclopropoxy)-7a-[2-fluoro-5-[(2,2,2-trifluoroacetyl)amino]phenyl]-4a,5,6,7-tetrahydro-4H-cyclopenta[d][1,3]thiazin-2-yl]benzamide (10.03 g, 19.2 mmol) in methanol (100 mL) and add 50% aqueous sodium hydroxide (5.46 mL, 96.2 mmol), stir and heat to 40° C. for 20 hours under nitrogen. Cool to ambient temperature and remove most of the organic solvent under reduced pressure. Dilute with water (200 mL) and DCM (300 mL) and stir until full dissolution occurs. Separate the layers and extract the aqueous layer with DCM (2×100 mL). Wash the combined organic extracts with water (4×100 mL), dry over magnesium sulfate, filter, and concentrate under vacuum to give the title compound as a pale yellow solid (4.69 g, 76%). ES/MS: m/z 322.0 (M+H).

EXAMPLE 1

N-[3-[(4aR,6S,7aS)-2-Amino-6-(cyclopropoxy)-4a,5,6,7-tetrahydro-4H-cyclopenta[d][1,3]thiazin-7a-yl]-4-fluoro-phenyl]-5-(1,2,4-triazol-1-yl)pyrazine-2-carboxamide

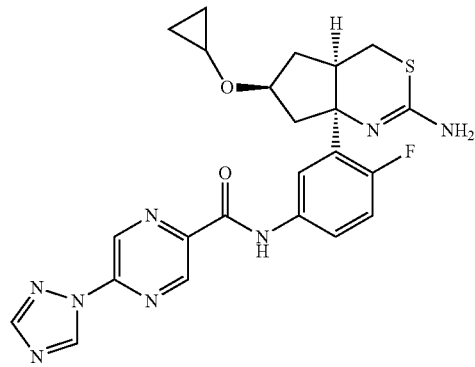 [SMILES: NC1=N[C@@]2(c3cc(NC(=O)c4cnc(-n5cncn5)cn4)ccc3F)C[C@@H](OC3CC3)C[C@H]2CS1]

Scheme 2, step 9: Add a solution of (4aR,6S,7aS)-7a-(5-amino-2-fluoro-phenyl)-6-(cyclopropoxy)-4a,5,6,7-tetrahydro-4H-cyclopenta[d][1,3]thiazin-2-amine (370 mg, 1.15 mmol) in methanol (19 mL) to 5-(1,2,4-triazol-1-yl)pyrazine-2-carboxylic acid (352 mg, 1.84 mmol) and HATU (759 mg, 1.96 mmol). Heat the resulting slurry to 70° C. and stir for 1 hour. Cool to room temperature and dilute with methanol to make a total volume of 19.6 mL. Filter the mixture and purify by reverse phase HPLC (CH$_3$CN and water with 10 mM ammonium bicarbonate adjusted to pH 9 with ammonium hydroxide, 30% to 100% $CH_3CN$ over 9 min at 60 ml/min) to obtain, after solvent evaporation, the title compound (341 mg, 60%). $^1$H NMR (400 MHz, $d_6$-DMSO): 10.86 (s, 1H), 9.58 (s, 1H), 9.22 (s, 1H), 9.24 (s, 1H), 8.49 (s, 1H), 7.77-7.84 (m, 2H), 7.14 (dd, J=8.8, 12.7 Hz, 1H), 5.84 (broad s, 2H), 4.26 (quintet, J=7.4 Hz, 1H), 3.24-3.29 (m, 1H), 2.80-2.81 (m, 2H), 2.37-2.45 (m, 1H), 2.07-2.14 (m, 1H), 1.86-1.96 (m, 2H), 0.41-0.50 (m, 4H), LCMS (ESI$^+$) m/z 495 [M+H]$^+$; OR $[\alpha]_D^{20}$+109.62 (c=10, $CHCl_3$).

In Vitro Assay Procedures:

To assess BACE1 selectivity over BACE2, the test compound is evaluated in FRET-based enzymatic assays using specific substrates for BACE1 and BACE2 as described below. For in vitro enzymatic and cellular assays, the test compound is prepared in DMSO to make up a 10 mM stock solution. The stock solution is serially diluted in DMSO to obtain a ten-point dilution curve with final compound concentrations ranging from 10 µM to 0.05 nM in a 96-well round-bottom plate before conducting the in vitro enzymatic and whole cell assays.

In Vitro Protease Inhibition Assays:

Expression of huBACE1:Fc and huBACE2:Fc

Human BACE1 (accession number: AF190725) and human BACE2 (accession number: AF 204944) are cloned from total brain cDNA by RT-PCR. The nucleotide sequences corresponding to amino acid sequences #1 to 460 are inserted into the cDNA encoding human $IgG_1$ (Fc) polypeptide (Vassar et al., *Science*, 286, 735-742 (1999)). This fusion protein of BACE1(1-460) or BACE2(1-460) and human Fc, named huBACE1:Fc and huBACE2:Fc respectively, is constructed into the pJB02 vector. Human BACE1 (1-460):Fc (huBACE1:Fc) and human BACE2(1-460):Fc (huBACE2:Fc) are transiently expressed in HEK293 cells. 250 µg cDNA of each construct are mixed with Fugene 6 and added to 1 liter HEK293 cells. Four days after the transfection, conditioned media are harvested for purification. huBACE1:Fc and huBACE2:Fc are purified by Protein A chromatography as described below. The enzymes are stored at −80° C. in small aliquots. (See Yang, et. al., *J. Neurochemistry*, 91(6) 1249-59 (2004).

Purification of huBACE1:Fc and huBACE2:Fc

Conditioned media of HEK293 cell transiently transfected with huBACE1:Fc or huBACE2:Fc cDNA are collected. Cell debris is removed by filtering the conditioned media through 0.22 µm sterile filter. 5 ml Protein A-agarose (bed volume) is added to 4 liter conditioned media. This mixture is gently stirred overnight at 4° C. The Protein A-agarose resin is collected and packed into a low-pressure chromatography column. The column is washed with 20× bed volumes of PBS at a flow rate 20 ml per hour. Bound huBACE1:Fc or huBACE2:Fc protein is eluted with 50 mM acetic acid, pH 3.6, at flow rate 20 ml per hour. One ml fractions of eluent are neutralized immediately with 0.5 ml 200 mM ammonium acetate, pH 6.5. The purity of final product is assessed by electrophoresis in 4-20% Tris-Glycine SDS-PAGE. The enzyme is stored at −80° C. in small aliquots.

BACE1 FRET Assay

Serial dilutions of the test compounds are prepared as described above. The compounds are further diluted 20× in $KH_2PO_4$ buffer. Ten µL of each dilution is added to each well on row A to H of a corresponding low protein binding black plate containing the reaction mixture (25 µL of 50 mM $KH_2PO_4$, pH 4.6, 1 mM TRITON® X-100, 1 mg/mL BSA, and 15 µM of FRET substrate based upon the sequence of APP) (See Yang, et. al., *J. Neurochemistry*, 91(6) 1249-59 (2004)). The content is mixed well on a plate shaker for 10 minutes. Fifteen µL of two hundred µM human BACE1(1-460):Fc (See Vasser, et al., *Science*, 286, 735-741 (1999)) in the $KH_2PO_4$ buffer is added to the plate containing substrate and the test compound to initiate the reaction. The RFU of the mixture at time 0 is recorded at excitation wavelength 355 nm and emission wavelength 460 nm, after brief mixing on a plate shaker. The reaction plate is covered with aluminum foil and kept in a dark humidified oven at room temperature for 16 to 24 hours. The RFU at the end of incubation is recorded with the same excitation and emission settings used at time 0. The difference of the RFU at time 0 and the end of incubation is representative of the activity of BACE1 under the compound treatment. RFU differences are plotted versus inhibitor concentration and a curve is fitted with a four-parameter logistic equation to obtain the $IC_{50}$ value. (May, et al., *Journal of Neuroscience*, 31, 16507-16516 (2011)).

The compound of Example 1 herein is tested essentially as described above and exhibits an $IC_{50}$ for BACE1 of 0.955±0.093 nM, n=6, mean±SEM; SEM=standard error of the mean. This data demonstrates that the compound of Example 1 inhibits purified recombinant BACE1 enzyme activity in vitro.

BACE2 TMEM27 FRET Assay

Transmembrane protein 27 (TMEM27) (Accession Number NM_020665), also known as Collectrin) is a recently described substrate for BACE2, but not BACE1 (Esterhazy, et al, *Cell Metabolism*, 14, 365-377 (2011)). To evaluate test compounds for inhibition of BACE2 enzymatic activity, a FRET peptide (dabcyl-QTLEFLKIPS-LucY) based upon the amino acid sequence of human TMEM27 is used as a substrate (Esterhazy, et al, *Cell Metabolism*, 14, 365-377 (2011)). Serial dilutions of the test compounds are prepared as described above. The compounds are further diluted 20× in $KH_2PO_4$ buffer. Ten µL of each dilution is added to each well on row A to H of a corresponding low protein binding black plate containing the reaction mixture (25 µL of 50 mM $KH_2PO_4$, pH 4.6, 1 mM TRITON® X-100, 1 mg/mL Bovine Serum Albumin, and 5 µM of TMEM FRET substrate). Fifteen µL of twenty µM human BACE2 (1-460):Fc (See Vasser, et al., *Science*, 286, 735-741 (1999)) in $KH_2PO_4$ buffer is then added to the plate containing substrate and the test compound to initiate the reaction. The content is mixed well on a plate shaker for 10 minutes. The RFU of the mixture at time 0 is recorded at excitation wavelength 430 nm and emission wavelength 535 nm. The reaction plate is covered with aluminum foil and kept in a dark humidified oven at room temperature for 16 to 24 hours. The RFU at the end of incubation is recorded with the same excitation and emission settings used at time 0. The difference of the RFU at time 0 and the end of incubation is representative of the activity of BACE2 under the compound treatment. RFU differences are plotted versus inhibitor concentration and a curve is fitted with a four-parameter logistic equation to obtain the $IC_{50}$ value. (May, et al., *Journal of Neuroscience*, 31, 16507-16516 (2011)).

The compound of Example 1 herein is tested essentially as described above and exhibits a BACE2 $IC_{50}$ of 87.3±11.1 nM, n=4, mean±SEM; SEM=standard error of the mean.

The ratio of BACE1 (FRET $IC_{50}$ enzyme assay) to BACE2 (TMEM27 FRET $IC_{50}$ assay) for Example 1 is about 91-fold, indicating functional selectivity for inhibiting the BACE1 enzyme. The data set forth above demonstrates that the compound of Example 1 is selective for BACE1 over BACE2.

SH-SY5YAPP695Wt Whole Cell Assay

The routine whole cell assay for the measurement of inhibition of BACE1 activity utilizes the human neuroblastoma cell line SH-SY5Y (ATCC Accession No. CRL2266) stably expressing a human APP695Wt cDNA. Cells are routinely used up to passage number 6 and then discarded.

SH-SY5YAPP695Wt cells are plated in 96 well tissue culture plates at $5.0 \times 10^4$ cells/well in 200 μL culture media (50% MEM/EBSS and Ham's F12, 1× each sodium pyruvate, non-essential amino acids and Na bicarbonate containing 10% FBS). The following day, media is removed from the cells, fresh media added then incubated at 37° C. for 24 hours in the presence/absence of test compound at the desired concentration range.

At the end of the incubation, conditioned media are analyzed for evidence of beta-secretase activity by analysis of Abeta peptides 1-40 and 1-42 by specific sandwich ELISAs. To measure these specific isoforms of Abeta, monoclonal 2G3 is used as a capture antibody for Abeta 1-40 and monoclonal 21F12 as a capture antibody for Abeta 1-42. Both Abeta 1-40 and Abeta 1-42 ELISAs use biotinylated 3D6 as the reporting antibody (for description of antibodies, see Johnson-Wood, et al., *Proc. Natl. Acad. Sci. USA* 94, 1550-1555 (1997)). The concentration of Abeta released in the conditioned media following the compound treatment corresponds to the activity of BACE1 under such conditions. The 10-point inhibition curve is plotted and fitted with the four-parameter logistic equation to obtain the $IC_{50}$ values for the Abeta-lowering effect. The compound of Example 1 is tested essentially as described above and exhibits an $IC_{50}$ of 0.38±0.14 nM, n=4 for SH-SY5YAPP695Wt A-beta (1-40) ELISA and an $IC_{50}$ of 0.43±0.08 nM, n=3 for SH-SY5YAPP695Wt A-beta (1-42) ELISA, (mean±SEM; SEM=standard error of the mean). The data set forth above demonstrates that the compound of Example 1 inhibits BACE1 in the Whole Cell Assay.

In Vivo Inhibition of Beta-Secretase

Several animal models, including mouse, guinea pig, dog, and monkey, may be used to screen for inhibition of beta-secretase activity in vivo following compound treatment. Animals used in this invention can be wild type, transgenic, or gene knockout animals. For example, the PDAPP mouse model, prepared as described in Games et al., *Nature* 373, 523-527 (1995), and other non-transgenic or gene knockout animals are useful to analyze in vivo inhibition of Abeta and sAPPbeta production in the presence of inhibitory compounds. Generally, 2 month old PDAPP mice, gene knockout mice or non-transgenic animals are administered compound formulated in vehicles, such as corn oil, beta-cyclodextran, phosphate buffers, PHARMASOLVE®, or other suitable vehicles via oral, subcutaneous, intra-venous, feeding, or other route of administration. One to twenty-four hours following the administration of compound, animals are sacrificed, and brains are removed for analysis of Abeta 1-x. "Abeta 1-x" as used herein refers to the sum of Abeta species that begin with residue 1 and end with a C-terminus greater than residue 28. This detects the majority of Abeta species and is often called "total Abeta". Total Abeta peptides (Abeta 1-x) levels are measured by a sandwich ELISA, using monoclonal 266 as a capture antibody and biotinylated 3D6 as reporting antibody. (See May, et al., *Journal of Neuroscience*, 31, 16507-16516 (2011)).

For acute studies, compound or appropriate vehicle is administered and animals are sacrificed at about 3 hours after dosing. Brain tissue, is obtained from selected animals and analyzed for the presence of Abeta 1-x. After chronic dosing brain tissues of older APP transgenic animals may also be analyzed for the amount of beta-amyloid plaques following compound treatment.

Animals (PDAPP or other APP transgenic or non-transgenic mice) administered an inhibitory compound may demonstrate the reduction of Abeta in brain tissues, as compared with vehicle-treated controls or time zero controls. For Example 1, three hours following a 3, 10, and 30 mg/kg oral dose of the compound to young female PDAPP mice, Abeta 1-x peptide levels are reduced approximately 22%, 42%, and 51% in brain hippocampus and 26%, 43%, and 59% in brain cortex p<0.01, compared to vehicle-treated mice.

Given the activity of Example 1 against the BACE enzyme in vitro, these Abeta-lowering effects are consistent with BACE inhibition in vivo, and further demonstrates CNS penetration of Example 1.

These studies show that the compound of the present invention inhibits BACE and is, therefore, useful in reducing Abeta levels.

I claim:

1. A compound of the formula:

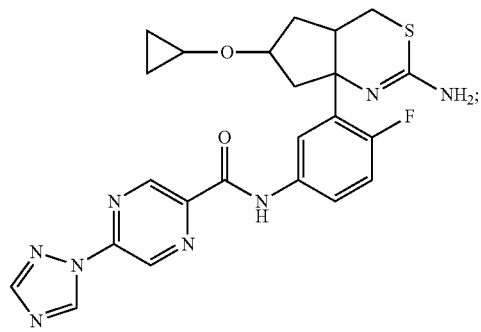 [SMILES: NC1=NC2(c3cc(NC(=O)c4cnc(-n5cncn5)cn4)ccc3F)CC(OC3CC3)CC2CS1]

or a pharmaceutically acceptable salt thereof.

2. The compound or salt according to claim 1 of the formula:

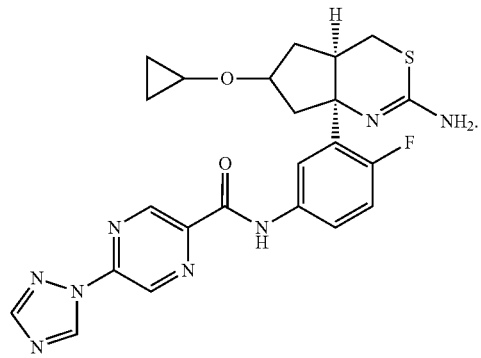 [SMILES: NC1=N[C@@]2(c3cc(NC(=O)c4cnc(-n5cncn5)cn4)ccc3F)CC(OC3CC3)C[C@H]2CS1]

3. The compound or salt according to claim 2 of the formula:

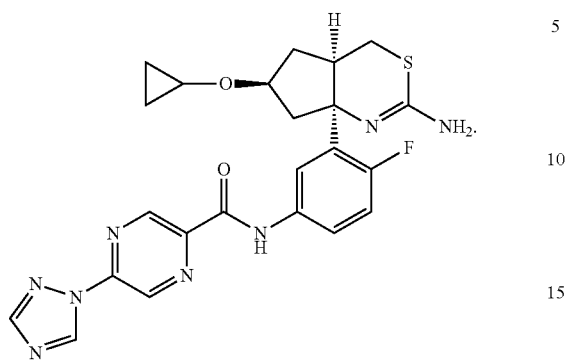

4. The compound according to claim 3 which is N-[3-[(4aR,6S,7aS)-2-amino-6-(cyclopropoxy)-4a,5,6,7-tetrahydro-4H-cyclopenta[d][1,3]thiazin-7a-yl]-4-fluoro-phenyl]-5-(1,2,4-triazol-1-yl)pyrazine-2-carboxamide.

5. A method of treating Alzheimer's disease in a patient, comprising administering to a patient in need of such treatment an effective amount of a compound of claim 1, or a pharmaceutically acceptable salt thereof.

6. A pharmaceutical composition, comprising a compound or a pharmaceutically acceptable salt thereof according to claim 1 with one or more pharmaceutically acceptable carriers, diluents, or excipients.

* * * * *